(12) United States Patent
McKnight et al.

(10) Patent No.: US 8,408,423 B1
(45) Date of Patent: Apr. 2, 2013

(54) METHOD AND APPARATUS FOR DISPENSING SANITIZER FLUID

(75) Inventors: Jacob McKnight, Argyll (GB); Virginia Gardiner, London (GB); Alexander R. Oshmyansky, Boston, MA (US)

(73) Assignee: Altitude Medical Inc, Boston, MA (US)

( * ) Notice: Subject to any disclaimer, the term of this patent is extended or adjusted under 35 U.S.C. 154(b) by 211 days.

(21) Appl. No.: 12/930,608

(22) Filed: Jan. 11, 2011

Related U.S. Application Data

(60) Provisional application No. 61/335,716, filed on Jan. 11, 2010.

(51) Int. Cl.
*B67D 1/07* (2006.01)
*B67D 7/06* (2010.01)
*B67D 3/00* (2006.01)
*G04C 23/42* (2006.01)
*A61L 2/00* (2006.01)

(52) U.S. Cl. ........ 222/192; 222/180; 222/504; 222/649; 422/292; 422/300

(58) Field of Classification Search .................. 222/192, 222/160, 207, 402.1, 180, 181.3, 504, 639, 222/649; 422/292, 306, 123, 300
See application file for complete search history.

(56) References Cited

U.S. PATENT DOCUMENTS

| | | | |
|---|---|---|---|
| 3,967,478 A | 7/1976 | Guinn | |
| 4,046,508 A | 9/1977 | McDonald | |
| 4,710,634 A | 12/1987 | Brookes | |
| 4,896,144 A | 1/1990 | Bogstad | |
| 5,454,409 A | 10/1995 | McAffer et al. | |
| 5,808,553 A | 9/1998 | Cunningham | |
| 6,029,600 A * | 2/2000 | Davis | 116/200 |
| 6,211,788 B1 | 4/2001 | Lynn et al. | |
| 6,289,557 B1 * | 9/2001 | Manson et al. | 16/412 |
| 6,577,240 B2 | 6/2003 | Armstrong | |
| 6,645,435 B2 | 11/2003 | Dawson et al. | |
| 6,874,697 B2 | 4/2005 | Callueng | |
| 7,080,427 B1 * | 7/2006 | Campopiano et al. | 16/110.1 |
| 7,320,418 B2 * | 1/2008 | Sassoon | 222/649 |
| 7,338,646 B2 * | 3/2008 | Gilbert | 422/292 |
| 2004/0223894 A1 | 11/2004 | Gilbert | |
| 2004/0237255 A1 * | 12/2004 | Lin et al. | 16/110.1 |
| 2006/0153733 A1 | 7/2006 | Sassoon | |
| 2006/0245818 A1 | 11/2006 | Stropkay et al. | |

FOREIGN PATENT DOCUMENTS

DE    198 57 268 A1    6/2000
WO    WO 2007/107784 A2    9/2007

OTHER PUBLICATIONS

International Search Report and Written Opinion dated Nov. 12, 2008 for PCT Application No. PCT/US2008/006505.
International Preliminary Report on Patentability dated Dec. 17, 2009 for PCT Application No. PCT/US2008/006505.
Supplementary European Search Report mailed Jun. 6, 2011 for Application No. 087546180.0—2113/2155266 (PCT/US2008006505).

* cited by examiner

*Primary Examiner* — Kevin P Shaver
*Assistant Examiner* — Stephanie E Williams
(74) *Attorney, Agent, or Firm* — Moser Taboada

(57) ABSTRACT

A method and apparatus for dispensing sanitizer fluid from a door handle. The apparatus includes a handle having a nozzle, an actuator fluidly coupled to the nozzle, and a cartridge of sanitizer fluid fluidly coupled to the actuator. Manipulation of the handle causes the actuator to dispense sanitizer fluid from the nozzle.

18 Claims, 4 Drawing Sheets

METHOD AND APPARATUS FOR DISPENSING SANITIZER FLUID

CROSS-REFERENCE TO RELATED APPLICATIONS

This application claims benefit of U.S. provisional patent application Ser. No. 61/335,716, filed Jan. 11, 2010, which is herein incorporated by reference.

BACKGROUND OF THE INVENTION

1. Field of the Invention

Embodiments of the present invention generally relate to a health care technology and, in particular, to a method and apparatus for promoting sanitization through door handles.

2. Description of the Related Art

Prevention of harmful diseases is a major concern for governments as well as various enterprises, such as multi-national corporations. If these diseases are not contained, an epidemic may ensue resulting in widespread panic and disorder among the population. For example, health care facilities, such as hospitals, may be overrun with patients straining the available medical professional workforce. In order to ensure a productive work and living environment, various enterprises and governments use various health care technologies, such as a sanitizer fluid, to stop the spread of pathogens that cause the harmful diseases. Such sanitizer fluids are generally dispensed via pump canisters located in bathrooms or via wall mounted pump canisters distributed throughout a building. Such sanitizer availability may not be convenient nor does availability guarantee use of the sanitizer fluid.

Therefore, there is a need in the art for a method and apparatus for dispensing sanitizer fluid in a very convenient manner, via door handles such that sanitizer fluid is conveniently available throughout a building.

SUMMARY OF THE INVENTION

Embodiments of the present invention include a method and apparatus for dispensing sanitizer fluid from a door handle. The apparatus comprises a handle having a nozzle, an actuator fluidly coupled to the nozzle, and a cartridge of sanitizer fluid fluidly coupled to the actuator. Manipulation of the handle causes the actuator to dispense sanitizer fluid from the nozzle onto a users hand.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
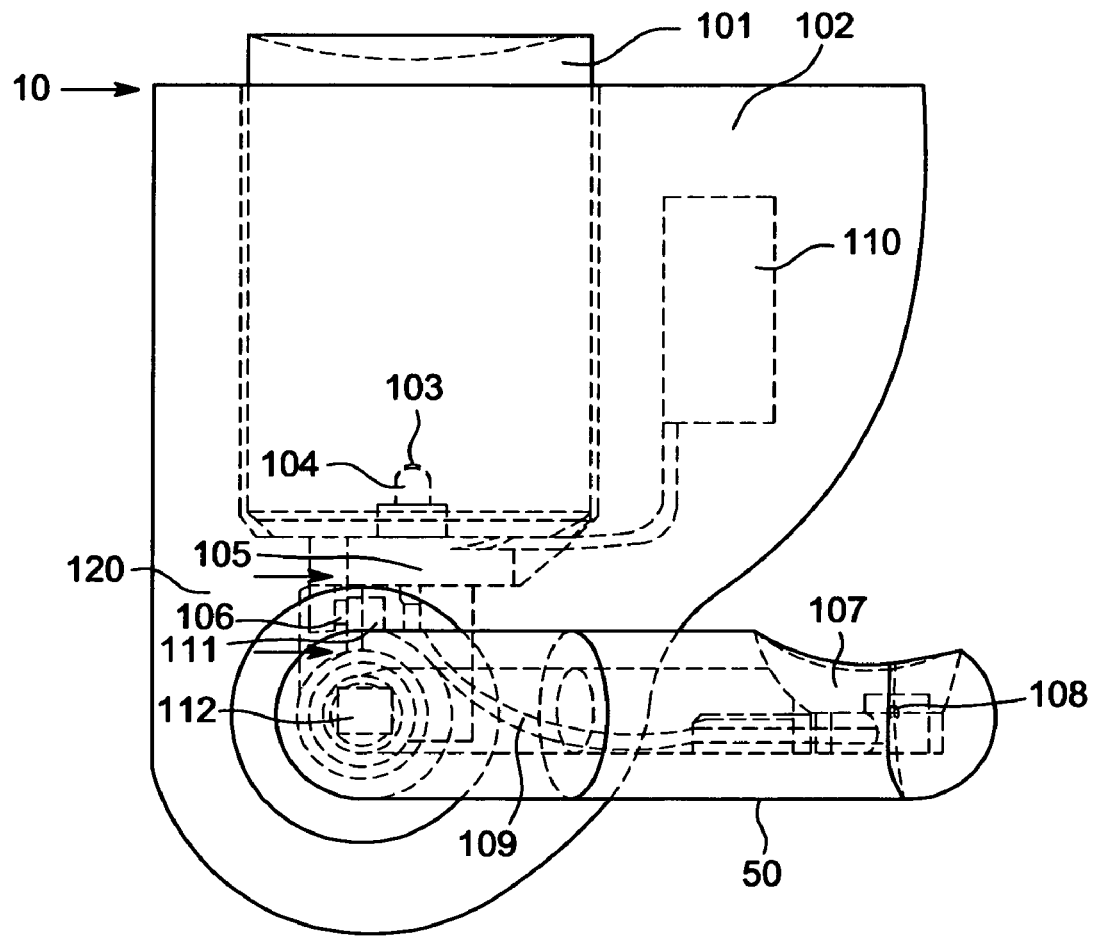
FIG. 1 depicts a front elevation view of a device to promote sanitization in accordance with one embodiment in the invention.

FIG. 1 depicts a front elevation view of a sanitizer agent dispensing device 10 to be fitted, via a standard spindle, to a standard latch mechanism of a common latching door. A cartridge 101 containing sanitizer fluid, such as pressurized alcohol, is slotted into a frame 102 which can be attached to a door and door latch. Although pressurized alcohol, is described as used in one embodiment of the invention, other types of sanitizing fluids based on or containing compounds with antibacterial, anti-viral, and/or anti-fungal properties, including but not limited to, ones based on: alcohol; benzochloronate; iodine; silver, silver-nitrate; TRIOSYN; and zinc, as well as combinations and compounds thereof, may be dispensed in various forms by the device 10, including but not limited to, in at least one of liquids, aerosols, sprays, streams and/or the like. The underside of the cartridge features a female valve 103 which connects to an actuator 120 comprising a male valve 104, a solenoid valve 105, a battery pack 110, a contact plate 111, and a pressure switch 106. The female valve 103 meets with a male valve 104 in the frame 102. When the cartridge 101 is slotted into the frame 102, the male valve 104 and the female valve 103 connect allowing pressurized alcohol to travel to the solenoid valve 105 attached to the male part of the valve 104. When the contact plate 111 is in the upright position (x-plane), it contacts a pressure switch 106 which holds the solenoid valve 105 shut. The solenoid valve 105 and pressure switch 106 are provided power by the battery pack 110 (e.g., one or more batteries) forming an electromechanical control system.

When the handle 50 is manipulated (e.g., rotated), the contact plate 111 rotates clockwise, releasing the pressure switch 106. The resulting signal from the pressure switch 106 opens the solenoid valve 105 for a uniform period of time allowing a standard quantity of pressurized alcohol to be released from the cartridge 101, through the female valve feature 103; the male valve 104 and the solenoid valve 105, into the connecting tube 109. The solenoid valve is controlled to open only for an amount of time necessary to dispense a uniform amount of sanitizer fluid. Such control may be facilitated by mechanical or electrical techniques. A sanitizer fluid, such as the pressurized alcohol 101, is carried through the connecting tube to a nozzle 108 where it is diffused into the indented region 107 of the handle 50 and onto the hand which is pushing the handle 50. The rotational movement of the handle 50 also rotates the spindle 112 which travels through the rear of the frame 102, allowing the device 10 to be mounted on any common door where the device 10 connects to the latching mechanism of the door via the spindle 112.

Figure 2:
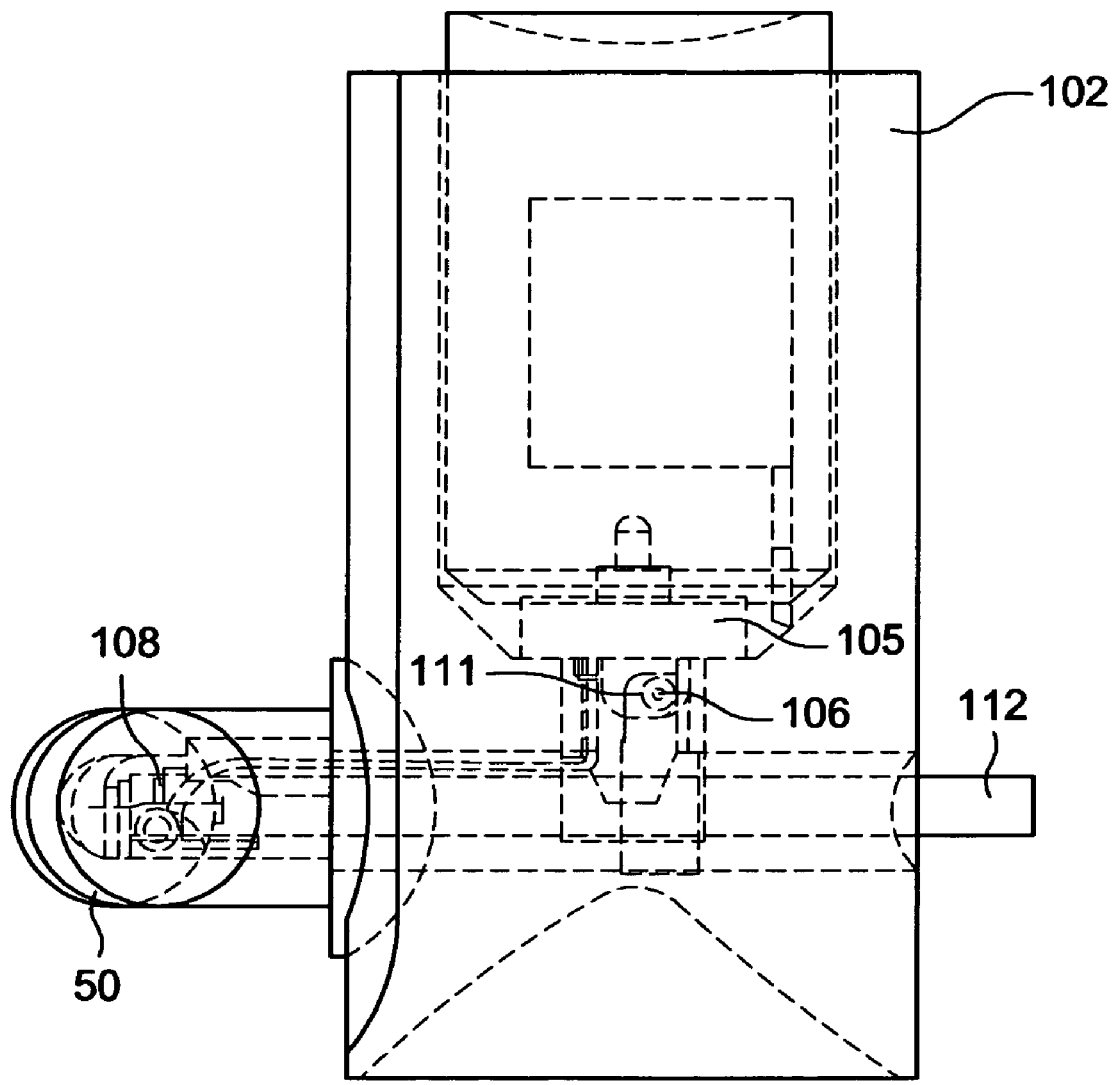
FIG. 2 depicts a side elevation view of the device to promote sanitization in accordance with one embodiment of the invention.

FIG. 2 depicts a side elevation view of the handle 50 that shows internal mechanisms. The spindle 112 is connected to the handle 50 and emerges from the back of the frame 102 to allow the handle 50 to be coupled to the latching mechanism of a common door (not pictured). Also visible are the switch 106 and contact plate 111, which operate the solenoid valve 105. When the handle 50 is rotated, the spindle 112 rotates, moving the contact plate 111 away from the switch 106, which in turn, triggers the opening of the solenoid valve 105, allowing sanitizing fluid to pass through the tube 109 to the nozzle 108 where it is sprayed upward onto the hand.

Figure 3:
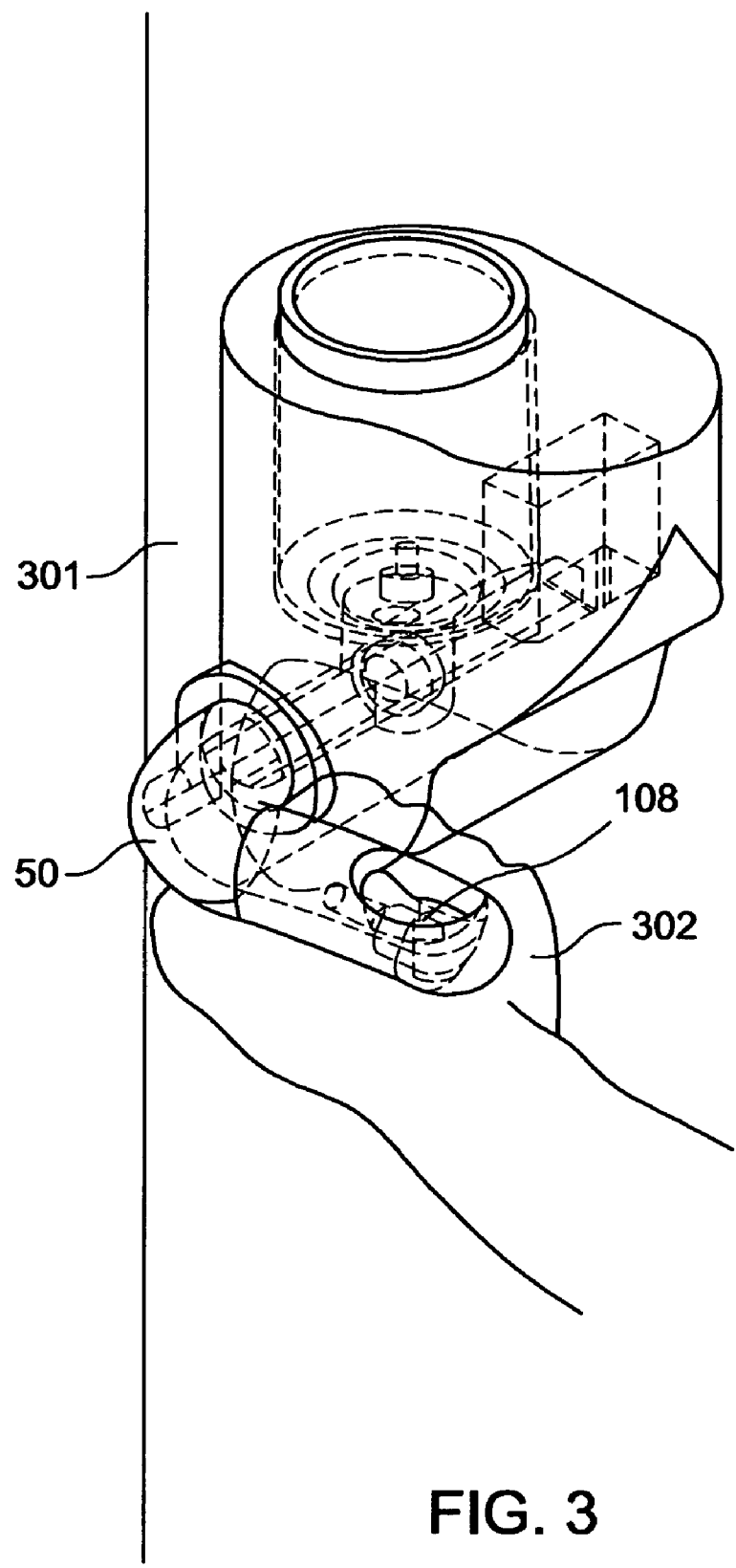
FIG. 3 depicts an isometric perspective view of a hand operating a handle according to one or more embodiments of the present disclosure.
Figure 4:
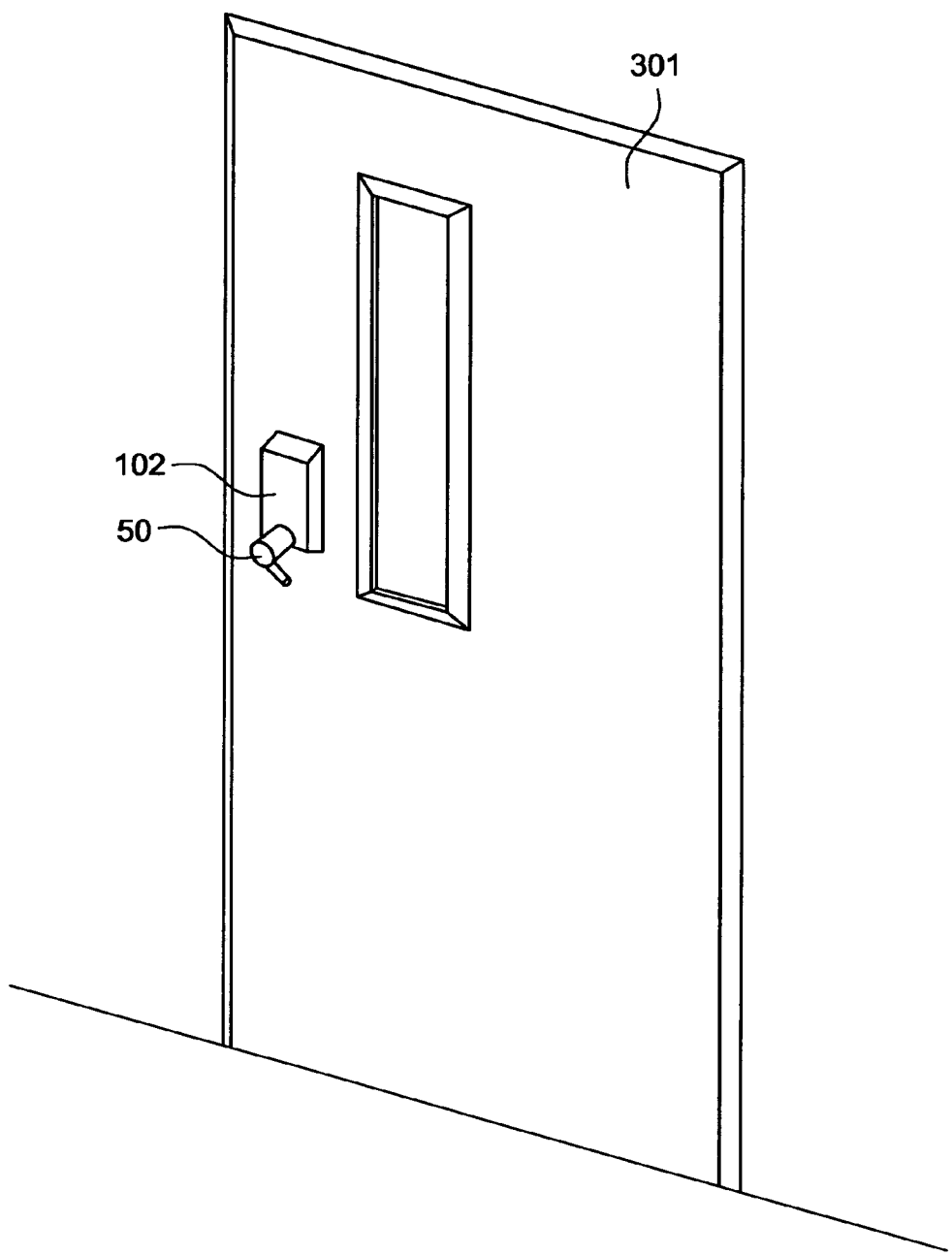
FIG. 4 depicts the device fitted to a door in accordance with one embodiment of the invention.

FIGS. 3 and 4 depict an isometric perspective view of the handle 50 mounted onto a door 301. In FIG. 3, a hand 302 can clearly be seen covering the handle 50. While the hand 302 is in this orientation, it is ideally positioned for the sanitizer fluid, such as the pressurized alcohol, to be issued from the nozzle 108 upward onto the hand 302 as the handle 50 is rotated to unlatch the door latch mechanism. This enables the user to then rub and spread the sanitizer fluid about the surface of both hands 302 in order to sanitize them.

While the foregoing is directed to embodiments of the present invention, other and further embodiments of the invention may be devised without departing from the basic scope thereof, and the scope thereof is determined by the claims that follow.

The invention claimed is:

1. An apparatus for dispensing sanitizer fluid comprising:
   a handle having a nozzle;
   an actuator fluidly coupled to the nozzle;
   a cartridge of sanitizer fluid fluidly coupled to the actuator;
   a first valve disposed within an underside of the cartridge;
   a second valve for coupling to the first valve;
   a solenoid valve coupled to the second valve;
   a power source for powering the solenoid valve; and
   a pressure switch for selectively coupling power to the solenoid valve in response to manipulation of the handle, where manipulation of the handle causes the actuator to supply sanitizer fluid from the cartridge to the nozzle.

2. The apparatus of claim 1, further comprising a frame supporting the handle, actuator, and cartridge.

3. The apparatus of claim 1, the handle further comprising:
   a spindle connected to the handle at a first end;
   an indented region located proximate a second end, opposite the first end, where the nozzle is proximate the indented region.

4. The apparatus of claim 3, wherein the handle is rotatable about the spindle.

5. The apparatus of claim 3, wherein rotation of the handle results in a corresponding rotation of the spindle.

6. The apparatus of claim 1, wherein the power source is a battery.

7. The apparatus of claim 1, wherein the actuator further comprises a contact plate contacting the pressure switch holding the solenoid valve shut while the handle is not being manipulated.

8. The apparatus of claim 1, wherein the released pressure switch opens the solenoid valve.

9. The apparatus of claim 1, wherein the solenoid valve is open for a pre-established period of time.

10. The apparatus of claim 1, the actuator further comprising:
    a solenoid valve coupled to the cartridge;
    a power source for powering the solenoid valve; and
    a pressure switch for selectively coupling power to the solenoid valve in response to manipulation of the handle.

11. The apparatus of claim 10, wherein the power source is a battery.

12. The apparatus of claim 10, wherein the actuator further comprises a contact plate contacting the pressure switch holding the solenoid valve shut while the handle is not being manipulated.

13. The apparatus of claim 10, wherein the released pressure switch opens the solenoid valve.

14. The apparatus of claim 10, wherein the solenoid valve is open for a pre-established period of time.

15. The apparatus of claim 1 wherein the sanitizer fluid comprises at least one of: a liquid, an aerosol, a spray, or a stream.

16. The apparatus of claim 1 wherein the sanitizer fluid comprises alcohol.

17. A method of dispensing sanitizer fluid, comprising:
    manipulating the handle of claim 1 to unlatch a door, where the manipulating causes an actuator to dispense sanitizer fluid from a cartridge to a nozzle in the handle.

18. The method of claim 17 wherein the manipulating simultaneously unlatches a door latch and dispenses sanitizer fluid from the nozzle.

* * * * *